United States Patent [19]

Walts et al.

[11] Patent Number: 4,923,810

[45] Date of Patent: May 8, 1990

[54] RESOLUTION OF GLYCIDYL ESTERS TO HIGH ENANTIOMERIC EXCESS

[75] Inventors: Alan E. Walts, Brookline, Mass.; Ellen M. Fox, Cranston, R.I.

[73] Assignee: Genzyme Corporation, Boston, Mass.

[21] Appl. No.: 236,616

[22] Filed: Aug. 24, 1988

[51] Int. Cl.$^5$ .................. C12P 17/00; C12P 17/02; C07P 41/00; C12N 9/20

[52] U.S. Cl. .................................. 435/117; 435/280; 435/157; 435/123; 435/132; 435/197; 435/176; 435/177; 435/198; 435/174; 435/180

[58] Field of Search ............. 435/280, 176, 180, 197, 435/157, 123, 198, 179, 132, 174, 814, 815, 177

[56] References Cited

U.S. PATENT DOCUMENTS

| | | | |
|---|---|---|---|
| 3,899,395 | 8/1975 | Moskowitz et al. | 435/198 |
| 3,901,763 | 8/1975 | Horiuchi et al. | 435/198 |
| 3,905,870 | 9/1975 | Kutzbach et al. | 435/815 |
| 4,006,059 | 2/1977 | Butler | 435/179 |
| 4,042,461 | 8/1977 | Esders et al. | 435/198 |
| 4,045,552 | 8/1977 | Kutzbach et al. | 435/815 |
| 4,226,938 | 10/1980 | Yoshida et al. | 435/176 |
| 4,421,850 | 12/1983 | Daniels et al. | 435/174 |
| 4,472,503 | 9/1984 | Matsuo et al. | 435/176 |
| 4,522,924 | 6/1985 | Tennent et al. | 435/174 |
| 4,668,628 | 5/1987 | Dahod et al. | 435/280 |
| 4,732,853 | 3/1988 | Whitesides et al. | 435/280 |

FOREIGN PATENT DOCUMENTS

| | | | |
|---|---|---|---|
| 0237080 | 9/1987 | European Pat. Off. | 435/123 |
| 2455017 | 12/1980 | France | 435/280 |
| 0138188 | 10/1979 | Japan | 435/197 |
| 0094295 | 6/1982 | Japan | 435/280 |
| 0183691 | 10/1984 | Japan | 435/180 |
| 1202688 | 9/1986 | Japan | 435/180 |
| 2061582 | 3/1987 | Japan | 435/174 |
| 8300345 | 2/1983 | PCT Int'l Appl. | 435/196 |
| 0703533 | 12/1979 | U.S.S.R. | 435/176 |
| 0935121 | 6/1982 | U.S.S.R. | 435/197 |
| 0943278 | 7/1982 | U.S.S.R. | 435/197 |

OTHER PUBLICATIONS

Cambou et al., J. Am. Chem. Soc., 106: 2687–2692 (1984).
Lavayre et al., Biotech. Bioeng., 24: 2175–2187 (1982).
Lavayre et al., Biotech. Bioeng., 24: 1007–1013.
Ladner, Wolfgong, E. and Whitesides, George M., "Lipase-Catalyzed Hydrolysis as a Route to Esters of Chiral Epoxy Alcohols"; J.A.C.S., vol. 106, 7250–7251 (1984).

Primary Examiner—Herbert J. Lilling
Assistant Examiner—Stephanie W. Zitomer
Attorney, Agent, or Firm—Lowell H. McCarter; Mark A. Hofer

[57] ABSTRACT

A method of resolving glycidyl esters to high enantiomeric excess involves fractionation of hydrolytic enzymes (e.g. lipases) to prepare biocatalysts with high enantioselectivity, and using these catalysts to selectively hydrolyze one enantiomer of the glycidyl esters. Also a method for fractionation includes stirring an aqueous solution of the enzyme with a solid inert adsorbent to provide an adsorbed and non-adsorbed enzyme fraction, where the non-adsorbed fraction displays a higher enantioselectivity than the crude non-fractionated enzyme. Also a composition composed of a glycidyl ester is obtained with an enantiomeric excess of greater than or equal to 97%.

12 Claims, No Drawings

RESOLUTION OF GLYCIDYL ESTERS TO HIGH ENANTIOMERIC EXCESS

BACKGROUND OF THE INVENTION

The present invention relates to a method for preparing optically active chiral epoxy alcohols and their carboxylic acid esters with high enantiomeric excess, via partial enzymatic hydrolysis of racemic carboxylic acid esters of chiral epoxy alcohols. More specifically the invention pertains to a method for producing these chiral epoxy alcohols and their carboxylic acid esters with a higher enantiomeric excess ("e.e.") than has been previously described. In addition, this invention relates to the new products of this resolution which have previously not been available in this substantially enantiomerically pure form via enzymatic resolution.

It has been previously proposed to employ partial enzymatic hydrolysis in the resolution of carboxylic acid esters of chiral epoxy alcohols, as described for example by W. E. Ladner and G. M. Whitesides in J. Am. Chem. Soc., Vol. 106, 7250–7251 (1984) and by W. E. Ladner and G.M. Whitesides in U.S. Pat. No. 4,732,853 (1988) hereby incorporated by reference. More specifically Ladner and Whitesides describe the use of hydrolytic enzymes in the resolution of esters of glycidol, and particularly of the butyrate ester of glycidol (glycidyl butyrate). According to their invention glycidyl butyrate can be resolved to a level of 93–95% enantiomeric excess via partial enzymatic hydrolysis of the racemic compound. We have found that the enantiomeric excess reaches a maximum at 93–95% and is not increased above this level by increasing the extent of hydrolysis.

Phillipi et al., 1987, Volume 2, pages 281–284 in O. M. Neijssel et al., Proc. 4th European Congress on Biotechnology, Elsevier, B. V., Amsterdam describe a separation of the porcine pancreatic lipase employed by Ladner et al. into three active fractions. Each of the distinct fractions displays a lower selectivity than the crude enzyme during partial hydrolysis of glycidyl butyrate, resulting in products with enantiomeric excesses of from 53–73%. These results suggest that methods for achieving very high selectivity (i.e. <95% e.e.) in the enzymatic resolution of carboxylic acid esters of chiral epoxy alcohols are not to be accomplished using fractions of crude enzyme.

The inability to obtain chiral epoxy alcohols with high enantiomeric excess limits the applicability of the products available according to the prior art. In many applications of the chiral epoxy alcohols and their carboxylic acid esters it is desirable to utilize material with an enantiomeric excess of greater than 95% and preferably of 98% or greater. In particular, when these compounds are used as starting materials in the syntheses of single-enantiomer pharmaceuticals the presence of more than 1% of the undesired isomer (i.e. less than 98% e.e.) is unacceptable due to potential toxicological problems arising from the wrong product isomer. Also, the presence of an undesired isomer may be problematic during purifications of advanced intermediates with multiple chiral centers due to diastereomer formation. The availability of a method to produce these chiral epoxides with high selectivity would greatly increase their utility in any of a number of applications.

SUMMARY OF THE INVENTION

In general the invention features, in one aspect, fractionation of a hydrolytic enzyme such as crude porcine pancreatic lipase via exposure of an aqueous solution of the crude enzyme to suitable inert adsorbents and thereby obtaining two fractions, one of adsorbed enzyme and one of non-adsorbed enzyme which remains in solution In another aspect the invention features the use of the fraction of non-adsorbed enzyme which remains in solution to effect the resolution of carboxylic acid esters of chiral epoxy alcohols, whereby a higher selectivity in the resolution is observed than when either the adsorbed enzyme or the crude non-fractionated enzyme is employed. In yet another aspect the invention features the unhydrolyzed carboxylic acid ester of a chiral epoxy alcohol which is obtained in greater than or equal to 97% e.e. according to any of the methods of the invention, and in addition features the resolved product alcohol which result from the enzymatic hydrolysis For purposes of the invention described herein, the phrase "inert adsorbent" refers to any solid matter which does not possess chemical moieties which react directly to form covalent bonds with proteins. Adsorption may occur by any of a number of phenomena including, but not limited to, interactions of hydrophobic or hydrophilic portions of a protein with like portions of the inert adsorbent, by hydrogen bonding, by salt bridge formation, or by electrostatic interactions. Examples of inert adsorbents include, but are not limited to, synthetic polymers (e.g. polystyrene, polyethylene, polyamides), mineralaceous compounds (e.g. glass, silica, sand, diatomaceous earth, Fuller's earth), naturally occurring polymers (e.g. cellulose), or metals (e.g. copper, iron, alloys, aluminates). The phrase "suitable adsorbent" refers to any of the above "inert adsorbents" which do not inactivate the enzymes when treated according to the methods of this invention. The increase in the observed product enantiomeric excess of from ca. 93% e.e. (obtained using non-fractionated enzyme) to ca. 97–98% e.e. (using the method of this invention) is substantial for two reasons. First, material with an e.e. equal to 97–98% e.e. is of much greater utility in synthesizing optically active pharmaceutical products than material with e.e. equal to 93%, since the former provides substantially purer products, with an e.e. which meets FDA standards for enantiomeric purity second, the change in e.e. of 4–5%, while of a small absolute magnitude, in fact represents a substantial change in the free energy ($\Delta\Delta G°$) associated with this selectivity. In particular, to increase the selectivity from 93 to 98% e.e. requires an energy input ($\Delta\Delta G°$) of almost 0.7 kcal. This same energy input would be sufficient to take a non-selective reaction (i.e. 0% e.e.) to 75% e.e. These numbers illustrate the phenomenon that as a reaction becomes more selective, the relative amount of energy required to achieve further increases in selectivity also increases Thus, the seemingly small increase of 4–5% in e.e. obtained using the invention described herein in fact represents a major improvement in the catalyst's ability to differentiate between the two enantiomers of glycidyl butyrate.

Ladner and Whitesides showed that, despite the known inactivating effect of epoxides on enzymes, racemic carboxylic acid esters of epoxy alcohols are enantioselectively hydrolyzed by enzymatic catalysis to form chiral epoxy alcohols in good yield together with chiral unhydrolyzed ester. The racemic carboxylic acid esters of chiral epoxy alcohols which can be employed in the process of the present invention include those having the following structure:

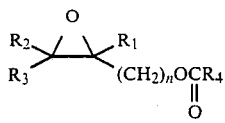

in which $R_1$, $R_2$ and $R_3$ are independently hydrogen or alkyl groups having 1 to 5 carbon atoms, $R_4$ is an alkyl group having 1 to 20 carbon atoms, preferably from 3 to 10 carbon atoms, either straight or branched chain, or an aryl group having 6 to 8 carbon atoms, and n is 1-5.

Any of the usual hydrolytic enzymes employed for enantioselective hydrolysis can be used in the present invention; among those which can be used are pig liver esterase, pancreatin, lipase s, such as steapsin (lipase from porcine pancreas extract), lipase from *Candida cylindracea*, lipase from *Rhizopus arrhizus*, cholinesterases such as acetyl cholinesterase, butyryl cholinesterase, and alpha chymotrypsin; of these, porcine pancreatic lipase is most preferred.

DESCRIPTION OF THE PREFERRED EMBODIMENT

The chiral epoxy alcohols and their carboxylic acid esters of the invention are obtained generally as follows. The racemic carboxylic acid ester of a chiral epoxy alcohol is mixed with water or aqueous buffer, and a suitable enzyme fraction prepared according to the invention is added to initiate hydrolysis. The enzyme fraction can be either (1) adsorbed enzyme fraction on the inert support, or, more preferably (2) the nonadsorbed enzyme fraction in the solution. The carboxylic acid formed during the hydrolysis is continuously neutralized via addition of base, and when the desired conversion is reached the product is isolated by extraction into an organic solvent.

The preferred method of fractionating the hydrolytic enzyme and using these fractions to make the chiral epoxy alcohols and their carboxylic acid esters of the invention will now be described in more detail. As one skilled in the art will appreciate, chiral epoxy alcohols and their carboxylic acid esters can be prepared using protocols that are within the method of the invention yet are different in particulars from those described here.

A preferred hydolytic enzyme, crude porcine pancreatic lipase, can be fractionated by exposure of an aqueous solution of the enzyme to any suitable inert adsorbent. The crude enzyme is first dissolved in water, and may or may not be buffered. The concentration of enzyme in water is not critical and can vary over a wide range such as 1 to 300 mg/mL, with a value of 100 mg/mL being typical. An inert adsorbent is then added to the enzyme solution and the solution is allowed to sit for a period of time (i.e. 1 to 4 hours) in order to effect the fractionation process.

Any of a number of inert adsorbents can be used, examples of which include synthetic polymers (e.g. polystyrene, polyethylene, polyamides), mineralaceous compounds (e.g. glass, silica, sand, diatomaceous earth, Fuller's earth), naturally occurring polymers (e.g. cellulose), or metals (e.g. copper, iron, alloys, aluminates). Celite® 521 diatomaceous earth and Amberlite® XAD-8 polymeric resin beads are most preferred. The ratio of adsorbent to enzyme affects the efficacy of fractionation, and the optimal ratio depends on the particular inert adsorbent being used. For example, when a diatomaceous earth adsorbent is employed (e.g. Celite® 521) a ratio of less than 2:1 Celite® adsorbent:enzyme (w:w) is used, with a ratio in the range of 0.5-1:1 (w:w) being preferred. When Amberlite® XAD-8 resin is employed as the adsorbent, a ratio of the polymeric resin to enzyme of 3:1 is preferred After contacting the enzyme with the adsorbent for a suitable period of time (generally 1 to 4 hours) the mixture is separated into the solid adsorbent and supernatant enzyme solution via filtration. At this point enzyme activity is present in both the supernatant solution and immobilized on the solid adsorbent, and either fraction can be used to effect the hydrolytic reaction. We have found, however, that the enantioselectivity of the enzyme remaining in the supernatant solution is greater than that of the enzyme immobilized on the adsorbent, and therefore the preferred fraction of the enzyme is that contained in the supernatant solution.

The actual resolution is then carried out using the general method described below employing the fractionated enzyme. The racemic carboxylic acid ester of a chiral epoxy alcohol is first mixed with water or aqueous buffer to provide a heterogeneous mixture. The ratio of substrate (racemic carboxylic acid ester) to water is not critical, and can vary from less than 1:100 to greater than 1:1, with values in the range of 1:4 to 1:1 being preferred. The appropriate enzyme fraction is then admixed with the substrate/water mixture and the entire mixture is stirred vigorously. As the reaction proceeds the carboxylic acid which is produced is continuously neutralized by adding base (e.g. aqueous sodium hydroxide). The hydrolysis can be allowed to proceed to any extent (e.g. 5-95%), however when the desired product is the carboxylic acid ester of the epoxy alcohol the hydrolysis is generally allowed to proceed to an extent greater than 50%, with a value of about 60% being preferred. Alternatively, when the desired product is the epoxy alcohol resulting from hydrolysis the reaction is generally allowed to proceed to a conversion of less than 50%, with about 30% being preferred. When the desired conversion is achieved the product is isolated from the reaction mixture via extraction with an organic solvent. When the fractionated enzyme is employed we have found that the carboxylic acid ester obtained at greater than 50% conversion is primarily the (R)-isomer, and in particular is obtained with higher enantioselectivity (e.g. greater than 95% e.e.) than when the crude enzyme is used.

Data for the enantiomeric excesses obtained using the methods of this invention are summarized in Table 1. While the results described here relate primarily to the resolution of glycidyl butyrate, the methods of this invention may be applied to any racemic carboxylic acid ester of a chiral epoxy alcohol as described by Ladner, et. al. in U.S. Pat. No. 4,732,853, (1988).

TABLE 1

| Example No. | Description | Product | Conversion (%) | Purity (%) | E.E. (%) |
| --- | --- | --- | --- | --- | --- |
| 1 | Supernatant (1:1 Celite:lipase) | (R)-g.b. | 65 | 93.4 | 98.2 |
| 1 | Solid Celite (1:1 Celite:lipase) | (R)-g.b. | 65 | 87.5 | 94.8 |

TABLE 1-continued

| Example No. | Description | Product | Conversion (%) | Purity (%) | E.E. (%) |
|---|---|---|---|---|---|
| 2 | Supernatant (0.5:1 Celite:lipase) | (R)-g.b. | 65 | — | 97.7 |
| 2 | Solid Celite (0.5:1 Celite:lipase) | (R)-g.b. | 63 | — | 97.1 |
| 2 | Supernatant (2:1 Celite:lipase) | (R)-g.b. | 65 | 86.6 | 95.9 |
| 3 | Supernatant (3:1 XAD-8:lipase) | (R)-g.b. | 65 | 91.6 | 97.4 |
| 3 | Solid Resin (3:1 XAD-8:lipase) | (R)-g.b. | 60.5 | 85.4 | 94.7 |
| 4 | Supernatant (3:1 XAD-8:lipase) | (R)-g.b. | 65 | 91.6 | 97.4 |
| 4 | Solid Resin (3:1 XAD-8:lipase) | (R)-g.b. | 60.5 | 85.4 | 94.7 |
| 4 | Supernatant (5:1 XAD-8:lipase) | (R)-g.b. | 65 | — | 96.2 |
| 4 | Supernatant (10:1 XAD-8:lipase) | (R)-g.b. | 62 | — | 93.4 |
| 4 | Solid Resin (10:1 XAD-8:lipase) | (R)-g.b. | 61 | 92 | 96.2 |
| 4 | Solid resin (3:1 XAD-8:lipase) | (S)-glycidol | 25 | — | 72.1 |
| 5 | Supernatant (1:1 Celite:lipase) | (R)-g.b. | 65 | 93.4 | 98.2 |
| 6 | Supernatant (1:1 Celite:lipase) | (R)-glycidol | 20 | 97.5 | 78.5 |
| 7 | Supernatant (1:1 Celite:lipase) | (R)-g.b. | 20 | 87.3 | 38.9 |
| 7 | Supernatant (1:1 Celite:lipase) | (S)-glycidol | 20 | 97.5 | 78.5 |
| 7 | Supernatant (1:1 Celite:lipase) | (R)-g.b. | 40 | 92.2 | 74.8 |
| 7 | Supernatant (1:1 Celite:lipase) | (R)-g.b. | 50 | — | 94.4 |
| 7 | Supernatant (1:1 Celite:lipase) | (R)-g.b. | 65 | — | 98.0 |
| 7 | Supernatant (1:1 Celite:lipase) | (R)-g.b. | 70 | — | 97.8 |
| 8 | Solid Celite (1:1 Celite:lipase) | (R)-g.b. | 65 | 87.5 | 94.8 |
| 9 | Supernatant (3:1 XAD-8:lipase) | (R)-g.b. | 65 | 91.6 | 97.4 |
| 10 | Solid | (R)-g.b. | 60.5 | 85.4 | 94.7 |

DETAILED DESCRIPTION OF THE INVENTION

The invention will now be described in more detail in the following examples are given by way of illustration and are not intended to limit the invention except as set forth in the claims.

For the purposes of these experiments activity units are defined as umol acid produced/min from glycidyl butyrate at ambient temperature (20°–23° C.).

EXAMPLE 1

In this example porcine pancreatic lipase was fractionated via exposure to Celite® 521 diatomaceous earth.

Porcine pancreatic lipase (20.0 g; 30 kU; Sigma type II) was dissolved in 150 mL of water in a 500 mL flask. Celite® 521 diatomaceous earth (20.0 g) was added to the aqueous mixture, followed by an additional 50 mL of water, and the entire mixture was stirred at room temperature for 1 hour. After this time the stirring was stopped and the solid was allowed to settle for 1 hour at room temperature. The supernatant was decanted from the mixture and the supernatant filtrate and residual solids (the diatomaceous earth with absorbed enzyme) were stored separately at 4° C. for future use. Both the supernatant filtrate and the residual Celite® were assayed with racemic glycidyl butyrate as substrate with the following results Supernatant: 42.3 U/mL, 8.5 kU total, 28% recovery from crude sample; Celite® adsorbent: 55.1 U/g, 3.3 kU total, 11% of crude sample. Data for the use of these fractions in the resolution of glycidyl butyrate are presented in Table 1.

EXAMPLE 2

In this example various ratios of Celite® 521 diatomaceous earth to porcine pancreatic lipase were used in the fractionation process.

Porcine pancreatic lipase (2.0 g; 3 kU; Sigma type II) was dissolved in 15 mL of water in a 50 mL flask. Celite® 521 diatomaceous earth (1.0 and 4.0 g corresponding to 0.5X and 2X the weight amount of lipase) were added, and the fractionation procedure was completed as in Example 1. The following activity numbers were obtained. 0.5X Supernatant: 110 U/mL, 2.2 kU total, 73% of original crude sample; 0.5X Celite diatomaceous earth adsorbent: 223 U/g, 405 U total, 14% of crude sample. 2X Supernatant: 62 U/mL, 1.2 kU total, 42% of original crude sample; 2X Celite diatomaceous earth adsorbent: 288 U/g, 1.7 kU total, 56% of original crude sample. Data for the use of these fractions in the resolution of glycidyl butyrate are presented in Table 1.

EXAMPLE 3

In this example porcine pancreatic lipase was fractionated via exposure to hydrophobic polymeric resin beads, i.e. Amberlite® XAD-8.

Porcine pancreatic lipase (50 g, 75 kU, Sigma type II) was dissolved in 340 mL of aqueous sodium phosphate (0.1 N, pH 8.0) in a 1000 mL flask. Amberlite® XAD-8 resin beads (150 g) were added and the mixture was stirred at room temperature for 3 hours. After this time the beads were separated either by filtration of the mixture through a Buchner funnel or by decanting the solution. The supernatant was either used directly in the resolution of glycidyl butyrate or stored at 4° C. for later use. The beads were washed with an additional 3 portions of phosphate buffer (500 mL each) and either used in the resolution or stored at 4° C. for late use. The supernatant filtrate and the bead resin were each assayed for activity with racemic glycidyl butyrate with the following results. Supernatant: 129 U/mL, 44 kU total, 58.5% of original crude enzyme activity; Resin: 35 U/g, 5.3 kU total, 7% of original crude enzyme activity Data for the use of these fractions in the resolution of racemic glycidyl butyrate are presented in Table 1.

EXAMPLE 4

In this example various ratios of Amberlite® XAD-8 resin to porcine pancreatic lipase were used in fractionation process.

Porcine pancreatic lipase (0.6 g, 900 U, Sigma type II) was dissolved in 4 mL of aqueous sodium phosphate (0.1 N, pH 8.0) in a 10 mL flask. Various quantities of Amberlite® XAD-8 resin (0.6, 2 and 3 g, corresponding to 1X, 3.3X, 5X and 10X the weight amount of lipase) were added and the fractionation procedure was completed as described in Example 3. The following activity numbers were obtained. 1X w/w Resin: 67 U/g, 40 U total, 4.4% yield; 3.3X w/w Supernatant (see Example 3); 3.3X Resin: 33 U/g, 66 U total, 7.2% yield; 5X w/w Supernatant: 35 U/mL, 243 U, 27% recovery; 5X Resin: 30 U/g, 91 U total 10% yield; 10X w/w Supernatant: 18 U/mL, 110 U, 12.2% recovery; 10X w/w Resin: 15 U/g, 90 U total, 10% yield. Data for the use of these fractions in the resolution of racemic glycidyl butyrate are presented in Table 1.

EXAMPLE 5

In this example the supernatant fraction obtained in Example 1 was used in the resolution of racemic glycidyl butyrate.

Racemic glycidyl butyrate (2.0 g) was mixed with 6 mL of water. The pH of the mixture was adjusted to 7.3 and a portion of the supernatant obtained in Example 1 (0.60 mL; 46 U) was added to the aqueous mixture The mixture was stirred vigorously while the pH was automatically maintained at 7.0–8.0 with a Chemcadet® pH controller via addition of 1.0 N aqueous NaOH. When 0.65 equivalents of NaOH had been added the reaction mixture was extracted with ether (3×50 mL). The combined organic extracts were washed with 10% aqueous HCl (1×150 mL), saturated aqueous sodium bicarbonate (1×150 mL) and brine (1×150 mL), and dried over anhydrous sodium sulfate. After evaporative removal of solvent the glycidyl butyrate product was analyzed by capillary gas chromatography (gc) for purity, and by high performance liquid chromatography (hplc) of a chiral derivative for enantiomeric excess as described by Phillipi et al., 1987, Volume 2, pages 281–284 in O. M. Neijssel et al., Proc. 4th European Congress on Biotechnology, Elsevier, B. V., Amsterdam. This material was of 93.4% purity (<1% glycidol) and contained a 98.2 enantiomeric excess of the (R)-enantiomer.

EXAMPLE 6

In this example the supernatant fraction obtained as in Example 1 was used in the resolution of racemic glycidyl butyrate and the product glycidol was isolated The procedure described in Example 5 for resolution of glycidyl butyrate was followed using 0.6 mL (47 U) of the supernatant fraction obtained as in Example 1. After the reaction had proceeded to 20% conversion the glycidol was isolated by extraction of the aqueous layer with ethyl acetate after prior removal of the glycidyl butyrate with ether. The glycidol obtained after distillation was of 97.5% purity, and consisted of a 78% excess of the (R)-enantiomer (see Table 1).

EXAMPLE 7

In this example racemic glycidyl butyrate was resolved to various conversion levels with the supernatant fraction obtained as in Example 1.

The procedure described in Example 5 for resolution of glycidyl butyrate was followed using the supernatant fraction obtained as in Example 1. After the reaction had proceeded to various conversion levels (e.g. 20–70%) the remaining glycidyl butyrate and/or glycidol product was isolated according to the standard work-up procedures in Examples 5 and 6. These products were analyzed for chemical purity and e.e. as described in Example 5 (Data in Table 1).

EXAMPLE 8

In this example the solid Celite ® diatomaceous earth fraction obtained as in Example 1 was used in the resolution of racemic glycidyl butyrate The procedure described in Example 5 for resolution of racemic glycidyl butyrate was followed except using 1.3 g of the solid Celite ® diatomaceous earth fraction obtained as in Example 1. The mixture was stirred vigorously and the pH was automatically maintained at 7.0–8.0 with a pH controller. The reaction proceeded to 65% conversion as measured by base addition. The glycidyl butyrate obtained after the standard work-up was found to be of 87.5% purity and consisted of a 94.8% excess of the (R)-enantiomer

EXAMPLE 9

In this example the supernatant fraction obtained as in Example 3 was used in the resolution of racemic glycidyl butyrate.

The procedure described in Example 5 for resolution of glycidyl butyrate was followed except using 2 mL (70 U) of the supernatant fraction obtained as in Example 3. After the reaction had proceeded to 65% conversion the remaining glycidyl butyrate was isolated according to the standard work-up procedure and found to consist of a 97.4% excess of the (R)-enantiomer.

EXAMPLE 10

In this example the solid resin fraction obtained as in Example 3 was used in the resolution of racemic glycidyl butyrate.

The procedure described in Example 5 for resolution of glycidyl butyrate was followed except using 1.8 g (62 U) of the solid resin fraction obtained as in Example 3. After the reaction had proceeded to 60.5% conversion the reaction mixture was decanted away from the resin and the remaining glycidyl butyrate was isolated according to the standard work-up procedure. This material contained a 94.7% excess of the (R)-enantiomer.

We claim:

1. In a method of making chiral epoxy alcohols or esters thereof which comprises providing a racemic carboxylic acid ester of an epoxy alcohol, bringing said ester into contact with water and a hydrolytic enzyme to hydrolyze said ester to the extent of about 5% to about 95%, and separating the resultant free alcohol from unhydrolyzed ester, the improvement wherein an aqueous solution of a crude hydrolytic enzyme is fractionated into an aqueous non-adsorbed enzyme fraction and an adsorbed enzyme fraction on an inert adsorbent before the non-adsorbed fraction is brought into contact with said ester.

2. The method as claimed in claim 1 in which said enzyme is lipase.

3. The method as claimed in claim 1 in which said racemic ester has the structures.

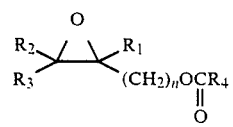

in which $R_1$, $R_2$ and $R_3$ are independently hydrogen or alkyl groups having 1 to 5 carbon atoms $R_4$ is an alkyl group having from 1 to 20 carbon atoms, preferably from 3 to 10 carbon atoms, either straight or branched chain, or an aryl group having 6 to 8 carbon atoms, and n is 1–5.

4. The method as claimed in claim 3 in which said enzyme is lipase.

5. The method as claimed in claim 4 in which the enzyme is porcine pancreatic lipase.

6. The method as claimed in claim 3 in which said racemic ester is a glycidyl ester.

7. The method as claimed in claim 4 in which said racemic ester is a glycidyl ester.

8. The method as claimed in claim 5 in which said racemic ester is a glycidyl ester.

9. The method as claimed in claim 1 including the additional steps of separately hydrolyzing said unhydrolyzed ester to provide a second free alcohol of opposite chirality to the first resultant free alcohol.

10. The method as claimed in claim 5 including the additional steps of separately hydrolyzing said unhydrolyze ester to provide a second free alcohol of opposite chirality to the first resultant free alcohol.

11. The method as claimed in claim 6 including the additional steps of separately hydrolyzing said unhydrolyzed ester to provide a second free alcohol of opposite chirality to the first resultant free alcohol.

12. The method of claim 1 wherein the inset adsorbent is selected from synthetic polymers, mineralaceous compounds, naturally occurring polymers or metals.

* * * * *